United States Patent
Rest et al.

(10) Patent No.: US 7,521,073 B2
(45) Date of Patent: Apr. 21, 2009

(54) COMPOSITIONS AND METHODS FOR ACTIVATING TOLL-LIKE RECEPTOR 4

(75) Inventors: Richard Rest, Rosemont, PA (US); Michael Karin, La Jolla, CA (US); Jin Mo Park, Charlestown, MA (US)

(73) Assignee: Philadelphia Health and Education Corporation, Philadelphia, PA (US)

( * ) Notice: Subject to any disclaimer, the term of this patent is extended or adjusted under 35 U.S.C. 154(b) by 0 days.

(21) Appl. No.: 11/764,469

(22) Filed: Jun. 18, 2007

(65) Prior Publication Data

US 2007/0248706 A1    Oct. 25, 2007

Related U.S. Application Data

(62) Division of application No. 11/248,085, filed on Oct. 12, 2005, now abandoned.

(60) Provisional application No. 60/617,894, filed on Oct. 12, 2004.

(51) Int. Cl.
*A61K 35/00* (2006.01)
*A61P 31/00* (2006.01)
*C12N 5/00* (2006.01)

(52) U.S. Cl. .................. 424/780; 435/7.8; 435/170; 435/375

(58) Field of Classification Search ................ 514/12.2; 536/350; 435/243, 252.1, 7.8, 170, 375; 424/780
See application file for complete search history.

(56) References Cited

U.S. PATENT DOCUMENTS

2006/0089305 A1   4/2006   Rest et al. .................... 514/12

OTHER PUBLICATIONS

Beutler et al., Innate immune sensing and its roots:the story of endotoxin, Nature Reviews 2003 3:169-176.
Collier et al., "Anthrax Toxin", Annu. Rev. Cell Dev. Biol. 2003 19:45-70.
Duesbery et al., "Proteolytic Inactivation of MAP-Kinase-Kinase by Anthrax Lethal Factor", Science 1998 280:734-737.
Giddings et al., "Redefining cholesterol's role in the mechanism of the cholesterol-dependent cytolysins", Proc. Natl. Acad. Sci. USA 2003 100(20):11315-11320.
Hsu et al., "The protein kinase PKR is required for macrophage apoptosis after activation of Toll-like receptor 4", Nature 2004 428:341-345.
Madden et al., "Cytolysin-Mediated Translocation (CMT): A Functional Equivalent of Type III Secretion in Gram-Positive Bacteria", Cell 2001 104:143-152.
Malley et al., "Recognition of pneumolysin by Toll-like receptor 4 confers resistance to pneumococcal infection", Proc. Natl. Acad. Sci. USA 2003 100(4):1966-1971.
Meehl et al., "Specificity of streptolysin O in cytolysin-mediated translocation", Molecular Microbiology 2005 52 (6):1665-1676.
Moayeri et al., "The roles of anthrax toxin in pathogenesis", Curent Opinion in Microbiology 2004 7:19-24.
Park et al., "Macrophage Apoptosis by Anthrax Lethal Factor Through p38 MAP Kinase Inhibition", Science 2002 297:2048-2051.
Paton, James C., "The contribution of pneumolysin to the pathogenicity of *Streptococcus pneumoniae*", Trends in Microbiology 1996 4(3):103-106.
Seong et al., "Hydrophobicity:an ancient damage-associated molecular pattern that initiates innate immune responses", Nature Reviews 2004 4:469-478.
Shannon et al, "Characterization of Anthrolysin O, the *Bacillus anthracis* Cholesterol-Dependent Cytolysin", Infection and Immunity 2003 71(6):3183-3189.
Shepard et al., "Identification of a Membrane-Spanning Domain of the Thiol-Activated Pore-Forming Toxin Clostridium perfringens Perfringolysin O: An alpha-Helical to Beta-Sheet Transition Identified by Fluorescence Spectroscopy", Biochemistry 1998 37:14563-14574.
Stassen et al., "Streptococcal Exotoxin Streptolysin O Activates Mast Cells To Produce Tumor Necrosis Factor Alpha by p38 Mitogen-Activated Protein Kinase-and Protein Kinase C-Dependent Pathways", Infection and Immunity 2003 71(11):6171-6177.
Tsukada et al., "Induction of Macrophage Interleukin-1 Production by *Listeria monocytogenes* Hemolysin", Cellular Immunology 1992 140:21-30.
Vitale et al., "Anthrax Lethal Factor Cleaves the N-Terminus of MAPKKs and Induces Tyrosine/Threonine Phosphorylation of MAPKs in Cultured Macrophages", Biochemical and Biophysical Research Communications 1998 248:706-711.

*Primary Examiner*—Chih-Min Kam
(74) *Attorney, Agent, or Firm*—Caesar, Rivise, Bernstein, Cohen & Pokotilow, Ltd.

(57) ABSTRACT

Methods for activating Toll-like receptor 4 via cholesterol-dependent cytolysins isolated from a Gram-positive bacteria are provided. In addition compositions containing an isolated cholesterol-dependent cytolysin or a fragment thereof or a mimetic of the cytolysin or fragment thereof and methods for use of such composition in inhibiting binding and/or interaction of Toll-like receptor 4 with endotoxin are provided. Methods for identifying modulators of Toll-like receptor 4 activation by a cholesterol-dependent cytolysin and use of such modulators in treatment of septicemia and/or septic shock are also provided.

1 Claim, No Drawings

US 7,521,073 B2

COMPOSITIONS AND METHODS FOR ACTIVATING TOLL-LIKE RECEPTOR 4

INTRODUCTION

This patent application is a divisional of U.S. patent application Ser. No. 11/248,085, filed Oct. 12, 2005, now abandoned, which claims the benefit of priority from U.S. Provisional Application Ser. No. 60/617,894 filed Oct. 12, 2004, which is herein incorporated by reference in its entirety.

This invention was supported in part by funds from the U.S. government (NIH Grant No. AI61712 and U54 AI57168). The U.S. government may therefore have certain rights in the invention.

FIELD OF THE INVENTION

The present invention relates to compositions comprising a member of the cholesterol-dependent cytolysin (CDC) family and methods of using these compositions to activate Toll-like receptor 4 and to identify modulators of Toll-like receptor 4 activation. Activation of Toll-like receptor 4 by endotoxin or lipopolysaccharide (LPS) can lead to septic shock or septicemia. Compounds identified as modulators, and more particularly inhibitors, of Toll-like receptor 4 activation by a member of the cholesterol-dependent cytolysin (CDC) family are expected to useful in the treatment of septic shock and/or septicemia. It is believed that isolated cholesterol-dependent cytolysins or fragments or mimetics thereof may inhibit the interaction of Toll-like receptor 4 and endotoxin or LPS as well.

BACKGROUND OF THE INVENTION

Toll-like receptors play pivotal roles in recognizing and resisting microbial infection (Kopp, E. and Medzhitov, R. Curr. Opin. Immunol. 2003 15:396-401; Beutler, B. and Rietschel, E. T. Nat. Rev. Immunol. 2003 3:169-176). Among the immediate outcomes of the TLR-dependent immune response is the production of cytokines by inflammatory cells such as macrophages. The production and release of such cytokines is responsible for the inflammatory response that accompanies bacterial infection. Toll-like receptor 4 (TLR4) activation by endotoxin or lipolysaccharide (LPS) produced by gram-negative bacteria leads to septic shock (Cohen, J. Nature 2002 420:885-891).

Infection of bone marrow derived macrophages with live B. anthracis (Sterne strain) has also been demonstrated to result in extensive apoptosis dependant on signaling from the LPS-responsive Toll-like receptor TLR4, which activates the proapoptotic double stranded (ds) RNA-dependent protein kinase PKR (Hsu et al. Nature 2004 428:341-345). However, *B. anthracis* is a Gram-positive bacterium that does not produce LPS.

In addition, the interaction of TLR4 with the cholesterol-dependent cytolysin pneumolysin was recently reported to be critically involved in the innate immune response to gram-positive *Pseudococcus* (Malley et al. Proc. Natl Acad. Sci 2003 100 (4):1966-1971). In particular, experiments were performed demonstrating that the inflammatory response of macrophages to pneumolysin was dependent on TLR4. Further, experiments with mutant mice lacking functional TLR4 revealed the mutant mice to be significantly more susceptible to invasive disease and death after exposure to pneumolysin-producing pneumococci when compared to control mice. Malley et al. thus concluded that the interaction of the pneumolysin with TLR4 is an important protective component of the host response to *Pseudococcus* (Malley et al. Proc. Natl Acad. Sci 2003 100 (4):1966-1971).

Cholesterol-dependent cytolysins (CDCs) are known to be major virulence factors in Gram-positive bacterial infections (Portnoy et al. Infect. Immun. 1992 60:1263-1267; Paton, J. C. Trends Microbiol. 1996 4:103-106; Rood, J. I. Annu. Rev. Microbiol. 1998 52:333-360). The mechanisms by which CDCs contribute to pathogenesis in Gram-positive infections have so far been attributed to their cytolytic activity and their role in regulating intracellular compartmentalization of pathogenic bacteria (Decatur, A. L. and Portnoy, D. A. Science 2000 290:992-995). For example, Listeriolysin O (LLO) from *Listeria* monocytogenes and Streptolysin O (SLO) from *Streptococcus* pyogenes have also been shown to activate macrophages and mast cells to produce proinflammatory cytokines and chemokines (Tsukada et al. Cell. Immunol. 1992 140:21-30; Stassen et al. Infect. Immun. 2003 71:6171-6177). In addition, Streptolysin O (SLO) from *Streptococcus* pyogenes has been shown to mediate vectorial transport of streptococcal proteins into the cytoplasm of host cells (Madden et al. Cell 2001 104:143-152; Meehl, M. A. and Caparon, M. G. Mol. Microbiol. 2004 52:1665-1676).

SUMMARY OF THE INVENTION

An aspect of the present invention relates to a method for activating Toll-like receptor 4 which comprises contacting Toll-like receptor 4 with a cholesterol-dependent cytolysin isolated from a Gram-positive bacteria.

Another aspect of the present invention relates to a method for identifying modulators of Toll-like receptor 4 activation which comprises measuring activation of Toll-like receptor 4 by a cholesterol-dependent cytolysin in the presence and absence of a test agent, wherein a change in activation of Toll-like receptor 4 in the presence of the test agent is indicative of the test agent being a modulator of Toll-like receptor 4 activation.

Another aspect of the present invention relates to compositions comprising an isolated cholesterol-dependent cytolysin or a fragment or mimetic thereof which inhibits binding and/or interaction of Toll-like receptor 4 with endotoxin.

Another aspect of the present invention relates to a method for treating septicemia or septic shock in a subject comprising administering to the subject a composition comprising an isolated cholesterol-dependent cytolysin or a fragment or mimetic thereof which inhibits binding and/or interaction of Toll-like receptor 4 with endotoxin.

Another aspect of the present invention relates to a method for treating septicemia or septic shock in a subject comprising administering to the subject an agent which inhibits activation of Toll-like receptor 4 activity by a cholesterol-dependent cytolysin.

Yet another aspect of the present invention relates to compositions for treatment of septicemia or septic shock comprising an agent which inhibits Toll-like receptor 4 activation by a cholesterol-dependent cytolysin.

DETAILED DESCRIPTION OF THE INVENTION

It has now been found that cholesterol-dependent cytolysins induce inflammatory and apoptotic responses in host immune cells via Toll-like receptor 4 (TLR4), a major contributor to Gram-positive induced septic shock.

Identification of a cholesterol-dependent cytolysin as a TLR4 agonist was first performed in *B. anthracis*.

In these experiments, *B. anthracis* cell wall preparations and culture supernatants were first tested for their ability to stimulate TNF-alpha gene expression and induce apoptosis of bone marrow-derived macrophages (BMDMs) in the presence of the p38 inhibitor SB202190. Treatment of BMDMs with a crude, commercially available, B. anthracis cell wall preparation did not strongly induce TNF-alpha mRNA expression or apoptosis. In contrast, the B. anthracis culture supernatant induced both TNF-alpha mRNA and apoptosis under the same conditions. The TNF-alpha- and apoptosis-inducing activity in the culture supernatant was sensitive to proteinase K digestion, indicating that a proteinaceous component is responsible for both activities. As only TLR4 agonists, but not agonists for other TLRs, can strongly potentates macrophage apoptosis in the presence of SB202190 (Park et al. Science 2002 297:2048-2051; Hsu et al. Nature 2004 428:341-345), this protein component was expected to act as a TLR4 agonist.

To identify this protein, the B. anthracis culture supernatant was sequentially purified through DEAE-Sepharose, Mono S, and phenyl-Sepharose chromatography columns. On the phenyl-Sepharose column, the TNF-alpha- and apoptosis-inducing activities cofractionated as a single peak centered at fraction 26. Analysis of the protein composition of the different column fractions revealed that a 63-kDa polypeptide copurified with both activities. Among the numerous secreted proteins predicted by the B. anthracis genome sequence to be present was anthrolysin O, a cholesterol-dependent cytolysin (CDC) encoded by the BA3355 gene (Shannon et al. Infect. Immun. 2003 71:3183-3189). The anthrolysin O polypeptide consists of 512 amino acids with the N-terminal 35 residues coding for a signal peptide, a size consistent with the 63-kDa band described above.

The phenyl-Sepharose fractions were thus analyzed by immunoblotting with anti-anthrolysin O antibody. It was found that anthrolysin O indeed co-purified with the 63-kDa protein, as well as the macrophage-stimulating and apoptosis-inducing activities.

To directly test whether anthrolysin O stimulated macrophages in a TLR4 -dependent manner, pure recombinant anthrolysin O was prepared by expression in E. coli. Treatment of BMDMs with recombinant anthrolysin O or other TLR agonists with different receptor specificities resulted in a strong induction of TNF-alpha mRNA. To compare the gene induction specificity of anthrolysin O to those of other TLR agonists, the mRNA levels of other cytokines including interleukin (IL)-1alpha, IL-Lβ, and IL-6 were examined. Whereas TNF-alpha was induced to similar extents by anthrolysin O and the different TLR agonists, the IL-1alpha and IL-6 genes were most strongly induced by anthrolysin O and LPS, but were less responsive to other TLR agonists. Furthermore, treatment of BMDMs with either anthrolysin O or the different TLR agonists in conjunction with SB202190 revealed that only anthrolysin O and LPS were able to cause a robust apoptotic response.

To specifically examine the role of TLR4 in the response to anthrolysin O, BMDMs were prepared from wild type (C3H/OuJ) and TLR4 mutant (C3H/HeJ) mice and their responses to anthrolysin O treatment were compared. Anthrolysin O induced activation of p38 MAPK and degradation of IKBα in TLR4 wild type, but not in TLR4 mutant BMDMs. The TLR4 mutant BMDMs showed no defect in their response to the TLR2 agonist synthetic bacterial lipopeptide. Anthrolysin O also failed to induce TNF-alpha and IL-6 gene expression in TLR mutant BMDMs. These observations indicate that anthrolysin O activates macrophages via TLR4.

To rule out the possibility that TLR4 activation by recombinant anthrolysin O is due to the presence of contaminating LPS in the preparation, BMDMs were treated with anthrolysin O, LPS, and taxol, another TLR4 agonist, in the presence of polymyxin B, which blocks LPS binding to TLR4. Activation of p38 MAPK by LPS, but not by anthrolysin O or taxol, was inhibited by polymyxin B. Polymyxin B treatment neutralized the activity of LPS at concentrations as high as 0.5 µg/ml.

Serum requirements for biological activity and the proteinase K sensitivity of anthrolysin O and LPS were also examined. TLR4 activation by LPS in vitro depends strictly on factors such as soluble CD14 and LPS-binding protein (LBP) that are provided by inclusion of serum (Ulevitch et al. Annu. Rev. Immunol. 1995 13:437-457). It was found that p38 MAPK activation in macrophages by recombinant anthrolysin O can occur in serum-free medium, in which LPS fails to activate p38 MAPK. The converse was observed after proteinase K digestion. Whereas proteinase K treatment completely abolished the ability of anthrolysin O to activate p38 MAPK, the activity of LPS was largely unaffected. Taken together, these experiments demonstrate that TLR4 activation by anthrolysin O is not due to contamination with LPS, whose activity is proteinase K-resistant and serum-dependent.

Anthrolysin O is closely related to other CDCs produced by Gram-positive pathogens. Accordingly, the ability of other CDCs produced by Gram-positive bacteria to activate TLR4 was examined. Listeriolysin O from Listeria monocytogenes and Streptolysin O from Streptococcus pyogenes, as well as perfringolysin O from Clostridium perfringens and anthrolysin O were produced by in vitro translation in reticulocyte lysates and added to BMDMs. All of the in vitro translated CDCs were found to activate iNOS expression by BMDMs, whereas a control lysate programmed with an empty backbone plasmid was inactive. Hence, all four CDCs are capable of activating macrophages.

Recombinant CDCs produced in and purified from E. coli were also examined for their dependence on TLR4 for macrophage activation. Treatment of TLR4 wild type BMDMs with increasing amounts of anthrolysin O, Listeriolysin O, Streptolysin O and perfringolysin O resulted in induction of TNF-alpha and IL-6 mRNAs. In most cases, the gene induction response reached its maximum at 100 ng/ml of CDC (or approximately 1.7 nM for an approximately 60 kDa protein). By contrast, TLR4 mutant BMDMs did not respond with cytokine gene expression to the same concentration of any of the CDCs. These results are indicative of the ability to activate TLR4 being a general property shared by CDCs from Gram-positive bacteria.

Thus, the present invention provides methods for activating Toll-like receptor 4 by contacting Toll-like receptor 4 with a cholesterol-dependent cytolysin isolated from a Gram-positive bacteria. In a preferred embodiment, the cholesterol-dependent cytolysin is Listeriolysin O (LLO) from Listeria monocytogenes, Streptolysin O (SLO) from Streptococcus pyogenes, perfringolysin O (PFO) from Clostridium perfringens, or anthrolysin O (ALO) from B. anthracis.

TLR4 is also known to bind to and/or interact with endotoxin. The ability of cholesterol-dependent cytolysins to bind with TLR4 is indicative of the potential utility of these proteins or fragments thereof or mimetics of these proteins or fragments thereof to inhibit binding and/or the interaction of TLR4 with endotoxin. Thus, it is expected that compositions comprising an isolated cholesterol-dependent cytolysin or a fragment thereof or a mimetic of these proteins or fragments thereof will be useful in treating septicemia and/or septic shock. Preferred cholesterol-dependent cytolysins or fragments thereof for use in these compositions are anthrolysin O, Listeriolysin O, Streptolysin O and perfringolysin O. Such compositions may further comprise acceptable carriers or vehicles for administration to a subject.

By "mimetic" it is meant to include both peptidomimetics and small organic molecules that bind to TLR4 in similar fashion to a cholesterol-dependent cytolysin, thereby inhibiting the ability of TLR4 to bind to and/or interact with endotoxin.

The present invention also provides methods for identifying modulators of a Toll-like receptor 4 activity which comprises measuring activation of Toll-like receptor 4 by a cholesterol-dependent cytolysin in the presence and absence of a test agent. In these methods, a change in activation of Toll-like receptor 4 activity in the presence of the test agent is indicative of the test agent being a modulator of a Toll-like receptor 4 activity.

Various assays for measuring TLR4 activation and/or identifying modulator of TLR4 activation can be used.

For example, a screening assay for TLR4 stimulation has been described wherein cells in culture are transfected with two plasmids, one carrying the gene for human TLR4 and the other, a detector plasmid, carrying a promoter that binds to NFkappa B upstream of a luciferase gene (Vogel, S. J. Biol. Chem. 2003 278:222506).

Alternatively a yeast two-hybrid system can be used for screening for TLR4 activation. With this system, two or three plasmids are transformed into a single yeast cell. In the positive control, one plasmid contains all or part of a gene for a cholesterol-dependent cytolysin such as anthrolysin O, and a second plasmid contains all or part of the TLR4 gene. These genes are transcribed and translated within the yeast cell. Binding of the cholesterol-dependent cytolysin to TLR4 is measured by a change in growth or color of the yeast. Inhibitors of this interaction can be identified by introduction of a third plasmid or screening of a library of small molecules encoded by DNA within a plasmid that bind to either the cholesterol-dependent cytolysin or to TLR4.

Another alternate or additional screening assay involves measuring the ability of an agent to bind to either recombinant TLR4 or a cholesterol-dependent cytolysin bound to a multiwell plate. Agents identified as having the ability to bind to either recombinant TLR4 or a cholesterol-dependent cytolysin can then be further tested for their ability to inhibit binding of TLR4 and cholesterol-dependent cytolysin.

Given the important role of activated TLR4 in endotoxin related septicemia and septic shock, it is expected that test agents identified as inhibitors of TLR4 activation in the above described methods of the present invention will be useful in preventing or treating endotoxin-related septicemia and/or septic shock.

Thus the present invention also provides methods and compositions for treating septicemia and/or septic shock in a subject by administering to the subject an agent which inhibits activation of Toll-like receptor 4 activity by a cholesterol-dependent cytolysin. Such methods and compositions may be used in subjects exhibiting symptoms of septicemia and/or septic shock. Such compositions and methods can also be used prophylactically in subjects at high risk for development of septicemia or septic shock including, but not limited to, patients undergoing major surgery, and in particular operations in the gut area, as well as immunosuppressed subjects undergoing surgical procedures.

The following nonlimiting examples are provided to further illustrate the present invention.

EXAMPLES

Example 1

Mice and Macrophages

C57BL/6J, C3H/OuJ, C3H/HeJ, B6.MRL-Tnfrsf6$^{1Pr}$/J (Fas1pr/1pr), and C57BL/6-Tnfrsf1a$^{tm1Imx}$ (TNFR1$^{-/-}$) mice were obtained from the Jackson Laboratory. IFNR1$^{-/-}$ mice in the 129/SvEv background were obtained from Dr. E. Raz (University of California, San Diego). BMDMs were prepared in accordance with procedures described by Park et al Science 2002 297:2048-2051.

Example 2

Reagents

B. anthracis cell walls were purchased from List Biological Laboratories, Inc. Other reagents used for treatment of BMDMs included: LPS (E. coli; Sigma), peptidoglycan (Fluka), poly(I-C) (Amersham Biosciences), CpG oligodeoxynucleotide (TIB MOLBIOL), Pam3CSK4 (EMC Microcollections), and R-848 (GLS Synthesis). SB202190 was from Calbiochem.

Example 3

Bacterial Strains, Culture and Infection

B. anthracis Sterne strain 7702 and its derivatives have been described by Shannon et al. infect. Immun. 2003 71:3183-3189). Bacteria were grown in brain heart infusion broth (BHI; Difco), without added bicarbonate, with shaking (200 rpm) at 37° C. in an air shaker incubator or on BHI agar in a humidified incubator. Bacterial infection of macrophage cultures was performed in accordance with procedures set forth by Hsu et al. (Nature 2004 428:341-345).

Example 4

Purification of Anthrolysin O from Bacterial Culture Supernatants

All buffers used in dialysis and column chromatography contained protease inhibitors (10 µM phenylmethylsulfonyl fluoride, 20 nM pepstatin A, 6 nM leupeptin, and 20 µM bisbenzamidine). To purify macrophage-stimulating activity from B. anthracis culture supernatants, bacteria were grown in BHI broth until OD595 reached 1.0. After removing bacteria by centrifugation, the supernatant (2 liters) was filtered through a 0.2 µm-pore Nylon filter set (Nalgene), concentrated up to 80-fold on a Centricon Plus-20 Filter Device (Millipore), and then dialyzed in buffer D100 (20 mM Tris-Cl [pH 7.0], 100 mM sodium chloride, and 0.1 mM EDTA). Proteins (84 mg) in the culture concentrate were applied to a DEAE-Sepharose column (10 ml) equilibrated with buffer D100. The macrophage-stimulating activity was found to pass through this column under this particular loading condition. Proteins in the flow-through fraction (61 mg) were equilibrated in buffer S50 (20 mM HEPES-KOH [pH7.0], 50 mM sodium chloride, and 0.1 mM EDTA) by dialysis and applied to a Mono S column (1 ml per 20 mg protein) equilibrated with buffer S50. After washing with buffer S50, bound proteins were eluted with a linear gradient of 50 to 1000 mM sodium chloride. The major peak fractions of macrophage-stimulating activity (3.1 mg) were pooled and mixed with an equal volume of 100 mM Tris-Cl (pH 7.0) and 3 M ammonium sulfate, and applied to a phenyl-Sepharose column (0.5 ml) equilibrated with buffer P1500 (50 mM sodium phosphate [pH 7.0], 1.5 M ammonium sulfate, and 0.1 mM EDTA). After washing with buffer P1500, bound proteins were eluted with an inverse linear gradient of 1.5 to 0 M ammonium sulfate. The phenyl-Sepharose fractions active in macrophage stimulation were stored at 80° C.

Example 5

Preparation of Recombinant Proteins

Recombinant LF, PA and CDCs were expressed in and purified from the E. *coli* strain BL21 (DE3) bearing the appropriate plasmid construct as described previously (Shannon et al. Infect. Immun. 2003 71: 3183-3189; Cunningham et al. Biochemistry 1998 37:15737-15746; Shepard et al. Biochemistry 1998 37:14563-14574). Purified LLO and LLO expression vector were provided by Dr. D. Portnoy (University of California, Berkeley, Calif.), and PFO and SLO expression vectors by Dr. R. Tweten (The University of Oklahoma Health Sciences Center, Oklahoma City, Okla.).

Example 6

Protein Analysis

Whole-cell extracts for immunoblot analysis were prepared with lysis buffer (20 mM HEPES-KOH at pH 7.6, 150 mM NaCl, 10% glycerol, 1% Triton X-100, 25 mM β-glycerophosphate, 2 mM EDTA, and protease inhibitors) and then subjected to SDS-PAGE. Proteins transferred to nitrocellulose membrane were probed with rabbit antiserum against recombinant anthrolysin O (Shannon et al. Infect. Immun. 2003 71: 3183-3189), and antibodies directed against actin (Sigma), iNOS, phospho-p38 a, p38 a, and I.Ba (all from Santa Cruz Biotechnology), and the immune complexes were visualized with the ECL Western blot reagent (Pierce).

Example 7

RNA analysis

Total RNA was isolated from BMDMs and RAW264.7 cells using the RNAwiz reagent (Ambion). For real-time PCR analysis, cDNAs were synthesized with the Superscript II reverse transcriptase system (Invitrogen). An amount of cDNA equivalent to 0.2 μg of total RNA was subjected to 40 cycles of PCR amplification consisting of a 15-second incubation at 95° C. and a 1-minute incubation at 60° C. Output was monitored using SYBR Green core reagents and the ABI Prism 7700 System (PE Applied Biosystems). The results were normalized to the level of cyclophilin mRNA.

Example 8

Measurement of Cell Viability

The TUNEL assay and Hoechst staining were performed as described (Park et al. Science 2002 297:2048-2051). The MTT assay was carried out using an MTT kit (Roche), according to the manufacturer's directions.

What is claimed is:

1. A method for measuring activation of Toll-like receptor 4 which comprises:
   providing a cell expressing Toll-like receptor 4;
   contacting the cell expressing Toll-like receptor 4 with an effective amount of a cholesterol-dependent cytolysin isolated from a Gram-positive bacteria; and
   measuring TNF-α mRNA;
   wherein activation of the Toll-like receptor 4 induces TNF-α mRNA production, and further wherein the cholesterol-dependent cytolysin is Listeriolysin O, Streptolysin O, perfringolysin O, or anthrolysin O.

* * * * *

UNITED STATES PATENT AND TRADEMARK OFFICE
CERTIFICATE OF CORRECTION

PATENT NO.        : 7,521,073 B2                                           Page 1 of 1
APPLICATION NO.   : 11/764469
DATED             : April 21, 2009
INVENTOR(S)       : Richard Rest et al.

It is certified that error appears in the above-identified patent and that said Letters Patent is hereby corrected as shown below:

Title Page, Item (73) Assignee, Should Read:   Philadelphia Health and Education Corporation, Philadelphia, PA (US)

The Regents of the University of California, Oakland, CA (US)

Signed and Sealed this

Twenty-fourth Day of November, 2009

David J. Kappos
*Director of the United States Patent and Trademark Office*